(12) United States Patent
Krumme et al.

(10) Patent No.: US 11,641,049 B2
(45) Date of Patent: May 2, 2023

(54) COMPACT INTEGRATED ROTARY JOINT WITH A RESONANT SHIELD

(71) Applicant: Schleifring GmbH, Fürstenfeldbruck (DE)

(72) Inventors: Nils Krumme, Feldafing (DE); Ulrich Herrmann, Munich (DE)

(73) Assignee: SCHLEIFRING GmbH, Fürstenfeldbruck (DE)

( * ) Notice: Subject to any disclaimer, the term of this patent is extended or adjusted under 35 U.S.C. 154(b) by 0 days.

(21) Appl. No.: 17/725,329

(22) Filed: Apr. 20, 2022

(65) Prior Publication Data
US 2022/0263208 A1 Aug. 18, 2022

Related U.S. Application Data

(63) Continuation of application No. PCT/EP2020/082123, filed on Nov. 13, 2020.

(30) Foreign Application Priority Data

Nov. 14, 2019 (EP) ..................................... 19209173

(51) Int. Cl.
*H01P 1/06* (2006.01)
*H05K 1/02* (2006.01)
(Continued)

(52) U.S. Cl.
CPC ............ *H01P 1/062* (2013.01); *H01F 38/18* (2013.01); *H01R 39/08* (2013.01); *H05K 1/0237* (2013.01); *H05K 1/0298* (2013.01)

(58) Field of Classification Search
CPC .. H01P 1/06; H01P 1/062; H01P 1/066; H01P 1/067; H01P 1/068; H01P 1/069; H01F 38/18
(Continued)

(56) References Cited

U.S. PATENT DOCUMENTS 5,530,424 A * 6/1996 Harrison et al. ......... A61B 6/56
378/4
7,717,619 B2 5/2010 Katcha et al.
(Continued)

FOREIGN PATENT DOCUMENTS

CN 207926288 U 9/2018
DE 102015121432 A1 6/2017
(Continued)

OTHER PUBLICATIONS

Trevisan et al., Wireless Sensing and Power Transfer in a Rotary Tool, In 2015 IEEE MTT-S International Microwave Symposium, pp. 1-4.
(Continued)

*Primary Examiner* — Benny T Lee
(74) *Attorney, Agent, or Firm* — Quarles & Brady, LLP; Yakov S. Sidorin

(57) ABSTRACT

A rotary joint includes a first part and a second part configured to rotate around a rotation axis against the first part. The first part has a first magnetic core and a capacitive data link component. The second part has a second magnetic core for coupling power with the a first magnetic core and a second capacitive data link component to transfer data from and/or to the first capacitive data link component. To weaken magnetic stray fields from the magnetic core, a resonant shield is provided outside the airgap between the magnetic cores. The resonant shield comprises an open ring-shaped structure, having two open ends which are connected by a capacitor to form a resonant circuit.

17 Claims, 11 Drawing Sheets

(51) Int. Cl.
*H01F 38/18* (2006.01)
*H01R 39/08* (2006.01)

(58) Field of Classification Search
USPC .......................................................... 333/261
See application file for complete search history.

(56) References Cited

U.S. PATENT DOCUMENTS

| | | | |
|---|---|---|---|
| 9,136,912 B2* | 9/2015 | West et al. | .............. H01P 1/068 |
| 2002/0057164 A1 | 5/2002 | Jin et al. | |
| 2016/0211701 A1* | 7/2016 | Krumme | .................. H05K 9/00 |
| 2016/0276871 A1 | 9/2016 | Schmitz et al. | |
| 2018/0037421 A1 | 2/2018 | Tam et al. | |

FOREIGN PATENT DOCUMENTS

| | | |
|---|---|---|
| EP | 2109866 B1 | 4/2015 |
| EP | 2933655 A1 | 10/2015 |
| EP | 2954844 A1 | 12/2015 |
| GB | 1321940 A | 7/1973 |

OTHER PUBLICATIONS

Trevisan et al., A UHF Near-Field Link for Passive Sensing in Industrial Wireless Power Transfer Systems, IEEE Transactions on Microwave Theory and Techniques, 2016, 64(5):1634-1643.
PCT International Search Report and Written Opinion, PCT/EP2020/082123, dated Feb. 10, 2021, 14 pages.

* cited by examiner

COMPACT INTEGRATED ROTARY JOINT WITH A RESONANT SHIELD

CROSS-REFERENCE TO RELATED APPLICATIONS

This application is a continuation of International Application No. PCT/EP2020/082123 filed on Nov. 13, 2020 and now published as WO 2021/094576, which designates the Unites States and claims priority form European Application No. 19209173.4 filed on Nov. 14, 2019. The disclosure of each of these patent applications is incorporated by reference herein.

RELATED ART

1. Field of the Invention

The invention relates to slipring devices and rotary joints for transmission of multiple electrical signals between rotating parts.

2. Description of the Related Art

Electrical sliprings and rotary joints are used to transfer electrical power and/or signals between a rotating and a stationary part. Such sliprings are used in different applications, like wind energy plants or computer tomography scanners. There are also many industrial, military, and aerospace applications in which sliprings are used.

Electrical sliprings and rotary joints should be compact, reliable, and affordable.

U.S. Pat. No. 7,717,619 discloses a rotary joint including inductive power transfer and capacitive data transfer. The capacitive data links are distant from the inductive power couplers. As this is a comparatively large rotary joint for CT scanners, spacing between the links is no problem.

EP 2 933 655 A1 discloses a compact rotary joint with inductive power transfer and capacitive data transfer. Here, capacitive couplers are arranged partially within the magnetic cores to save space. This is acceptable, because only a low bandwidth for control signals is required.

EP 2 109 866 B1 discloses a shielded power coupling device capable of reducing radio frequency (RF) emission and/or other electromagnetic interference. Here circular mechanical and electrically conductive parts are arranged to eliminate interference by cancellation of electromagnetic fields.

Here, the shield has a wide bandwidth and therefore may also affect components. Dependent on the size, the shield may have a resonance frequency in a range of several 100 MHz and therefore may radiate signals from capacitive data links.

As the shield has a wide bandwidth with nearly no losses in the operating frequency range of the power transformer, such shield is of advantage for keeping stray fields from sensitive electronic components. But since there are no losses, the stray field is shifted spatially, but unwanted energy is not absorbed, which—especially with a contactless link in close proximity this—is a major disadvantage.

SUMMARY OF THE INVENTION

The embodiments are providing a compact rotary joint providing at least inductive power transfer and capacitive data transfer with a high data rate.

Solutions of the problem are described below.

In an embodiment, a slipring device comprises a first part and a second part which are rotatable against each other about a center axis. For example, the first part may be stationary, whereas the second part may be rotating relative thereto. Of course, the rotating and stationary parts may be exchanged or even both parts may be rotating with different speeds. Also the arrangement may be axially displaced and act as a connector, providing power and date transmission as long as the air gap between both parts is within a working distance.

The first part may have a first housing which may contain first rotary joint components like inductive coupling components, capacitive coupling components and slip rings. Inductive coupling components may be used for power transfer and sometimes for data transfer. Capacitive coupling elements may be used for data transfer and in rare cases for power transfer. The first part may also have an antenna together with modulator and/or demodulator to allow wireless transmission in the near field at low radiated energy. These components may be arranged on a first printed circuit board which may have a sliding track as a PCB trace, and/or a brush mounted and/or soldered to the PCB.

The second part may have a second housing which may contain second rotary joint components like inductive coupling components, capacitive coupling components and slip rings. These components may be arranged on a second printed circuit board which may have a sliding track as a PCB trace, and/or a brush mounted and/or soldered to the PCB.

The rotary joint components in the first part and the second part are designed such that these components interface in a way to form inductive, capacitive, wireless radio frequency (rf) or sliding contact connections. Therefore, a contact brush at the first part may interface with a sliding track at the second part and/or a contact brush at the second part may interface with a sliding track at the first part. An inductive coupler at the first part may interface with an inductive coupler at the second part and a capacitive coupler at the first part may interface with a capacitive coupler at the second part. An rf antenna at the first part may interface with an rf antenna at the second part. There may be multiple connections between the first part and the second part.

For holding the first part and the second part in a spatial relationship and allowing rotation therebetween, preferably at least one bearing is provided. Such a bearing may be a slide bearing, a ball bearing, a liquid bearing, or any other suitable bearing. Preferably, a ball bearing and most preferably two ball bearings are provided.

An embodiment relates to a disk-shaped rotary joint, also referred to as a "platter" rotary joint. Here, the main components may be approximately arranged in or close to a common plane. Such a plane may be orthogonal to the rotation axis.

In this embodiment, a rotary joint includes an inductive coupling component, further including at least a first magnetic core on the first part and a second magnetic core on the second part. The magnetic cores may include ferrite material, iron material, or any other winding-suitable soft-magnetic material. A gap, which may have a constant width and which may have a circular outer contour is formed between the at least one first magnetic core and the at least one second magnetic core.

Within the first magnetic core is a first winding, and within the second magnetic core is a second winding. The first winding and the second winding are magnetically coupled with each other through the first magnetic core and the second magnetic core. While one of the windings may be connected to an AC signal generator, the other winding may be connected to a rectifier for delivering power to a circuit connected to the winding.

In an embodiment, with a disk-shaped arrangement of the magnetic cores, at least one resonant shield is provided radially outside the airgap of the magnetic core. In an embodiment, with a cylinder (or drum)-shaped arrangement of the magnetic cores, at least one resonant shield is provided axially outside the airgap of the magnetic core. Each resonant shield comprises an open ring shaped structure. The ring shaped structure has two open ends which are coupled to and connected by a capacitor to form a resonant circuit. The resonance frequency is determined by the inductance of the ring shaped structure and the capacitance. This resonant circuit may have a resonance frequency which is at an operation frequency of the first and second magnetic core or multiples thereof. The embodiment may also work for a variety of frequencies, for example if the resonant frequency is very low (e.g. below the lowest usable frequency). The resonant frequency may be lower than one magnitude below the lowest operation frequency. Such a dimensioning provides a constant attenuation over a broader range of operational frequencies without any peaks. An operation frequency of an inductively coupled power transmission typically ranges between 40 and 300 kHz.

The resonance shields have the best effect, if their open ring shaped structures are comparatively close to the source of the magnetic field. Tests have shown that the open ring shaped structures may be closer to a magnetic core than a maximum dimension of a magnetic core for best efficiency. Efficiency is further increased, if the distance of the open ring shaped structures to an air gap is closer than one of 10 times, 5 times, 2 times the size of the air gap.

Such a resonant shield may essentially cancel the stray fields from the airgap and/or the first or second magnetic core. It may at least cancel more than 50%, more than 60%, more than 70%, more than 80%, more than 90% or more than 95% of the stray field.

In an embodiment, two resonance shields are spaced apart equal or more than the width of the airgap.

In another embodiment, at least one resonance shield has a resonance frequency differing from another resonance shield. Combining multiple resonance shields with slightly different resonance frequencies results in a more broadband behavior. The resonance frequency may be less than 20% above, at or below an operation frequency of the first and second magnetic core or multiples thereof.

In another embodiment the resonance shield may be additionally loaded by a resistor to increase damping of the resonance circuitry, thereby widening the frequency range where the resonance shield is effective having a low impedance.

In another embodiment, at least one resonance shield includes multiple windings which increases inductance and may allow for smaller capacitor values. In an embodiment, at least one galvanic slipring connection is provided by at least one sliding brush at the first part being in galvanic contact with at least one sliding track at the second part. To improve contact and reduce noise and resistance, multiple sliding brushes may be provided. The galvanic contact may be used for grounding of the circuit. There may be multiple slipring connections, further, brush and track may be exchanged.

In addition, at least one data link may be provided, which may be at least one of a capacitive data link, an inductive datalink, and wireless link (e.g. Bluetooth, WiFi, WLAN).

In an embodiment including a capacitive data link, the capacitive data link may include a first capacitive data link component on the first part in correspondence with a second capacitive data link component on the second part. One of these capacitive data links may be a unidirectional component for transmitting data, whereas the other component may be a unidirectional component for receiving data. In an alternative embodiment, both components may be bidirectional components for transmitting and receiving data. If at one part, a unidirectional component for transmitting data is provided, corresponding thereto on the second part, a unidirectional component for receiving data is provided, and vice versa. There may be multiple capacitive data links.

In an embodiment including an inductive data link, the inductive data link may use the same magnetic cores as used for power transmission preferably with separate first and second windings for power and for data transmission, allowing a unidirectional or bidirectional transmission and reception of data. If at one part, a unidirectional component for transmitting data is provided, corresponding thereto on the second part, a unidirectional component for receiving data is provided, and vice versa. This inductive transmission link may be placed in the close proximity to the power core and the electronic circuitry requiring shielding of the stray field generated by the inductive power transmission.

The same considerations, however, apply also if a wireless data transmission is realized, including a modulator and a demodulator circuitry which is also prone to noise induced by the stray field of the power transmission cores. By lowering the interference of the contactless power transmission the field strength of the near field wireless communication can be further reduced. The magnetic cores may be arranged radially closer to the rotational axis, which is also the center axis of the rotary joint, than the galvanic slipring connection and the at least one capacitive data link. There may be a free bore around the center axis, such that other components like optical rotary joints or media rotary joints may be fed through the rotary joint. The magnetic core may have an inner diameter in the range of 1 cm to 2 m, depending on the requirement and the size of the rotary joint. In an embodiment, the magnetic core has an inner diameter between 5 cm and 10 cm and an outer diameter between 8 cm and 15 cm. The width of the magnetic core is determined by the size of the required magnetic material and may be in the range from 2 cm to 20 cm. The magnetic core may include ferrite material, iron material, or any other suitable soft-magnetic material. The capacitive data links are arranged outside of the magnetic cores and they may be arranged distant from the magnetic cores to avoid interference by the magnetic fields of the magnetic cores.

A galvanic slipring contact may be arranged between the magnetic cores and the at least one capacitive data link. This increases the distance between the at least one capacitive data link and the magnetic cores without wasting space and thereby reduces interference.

Interference between the magnetic cores and the at least one capacitive data link is a critical design issue, as the capacitive data links have only a very weak coupling between the two parts, due to a very small coupling capacitance in the range of a few Picofarad (pF), and the magnetic cores handle comparatively high power levels. Signals coupling from the magnetic cores into the at least one capacitive data link may affect the signals coupled in the capacitive data link. Specifically, in compact rotary joints, space and costs are critical design issues. Therefore, the magnetic cores are normally designed in such a way that the magnetic field strength and therefore the magnetic flux in the magnetic cores are dimensioned such that the value of such flux is close to the maximum flux of the magnetic material. If a magnetic core is operated with a flux that is close to the maximum flux of the material of such magnetic core, such magnetic core starts to produce magnetic flux outside of the core, thus generating a magnetic field protruding from the core to the surrounding environment and therefore also protruding into other components of the rotary joint. The effects of this stray field may be reduced by separating the components which would further increase the size of the rotary joint, which is not desired. Therefore, a shielding may be provided to reduce the interference of the magnetic field with the capacitive data links. Such a shield should be simple, inexpensive and should not consume much space. Therefore, providing a further housing around the magnetic core for providing additional shielding or at least reducing the stray field is not desired.

In this embodiment, placement of the galvanic contact system between the magnetic cores and the at least one capacitive data link will further reduce the stray field, because the field exiting the core and going through the environment of the core may cross the galvanic sliding contact system and specifically the galvanic sliding track. A galvanic sliding track normally is a closed ring of a low resistance conductive structure, in which the magnetic fields generate eddy currents, which leads to a weakening of the magnetic field. This weakening process further reduces interference with the at least one capacitive data link. To improve this effect, the sliding track may be increased in size, preferably in width, but also in thickness, which would further lead to a higher current capacity of the sliding contact system. The galvanic contact system may be in a plane between the magnetic cores. The galvanic contact system may be close to an air gap between the magnetic cores. At least one sliding track may be arranged below a plane defined by the air gap between the magnetic cores and at least one sliding brush is mounted above the plane. This plane may be the same as the common plane mentioned above or, alternatively, be different from the common plane, if for example the magnetic cores have an axial offset to the capacitive data links.

BRIEF DESCRIPTION OF THE DRAWINGS

In the following the invention will be described by way of example, without limitation of the general inventive concept, on examples of embodiment with reference to the drawings.

Figure 1:
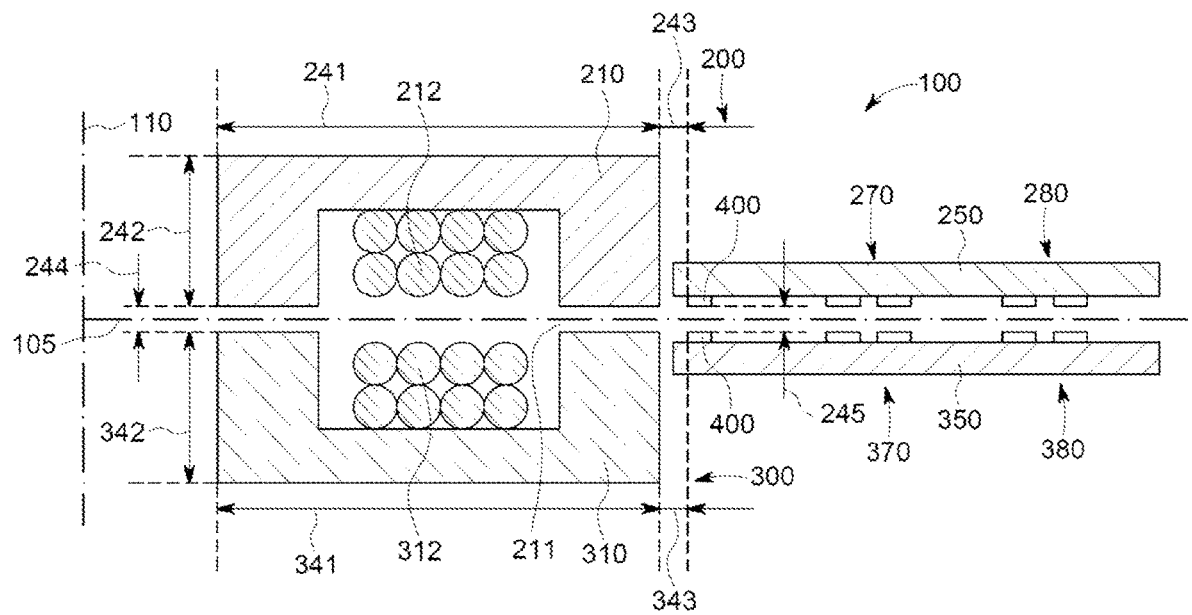
FIG. 1 shows a sectional view of a rotary joint.

Generally, the drawings are not to scale. Like elements and components are referred to by like labels and numerals throughout the detailed description of the drawings. For the simplicity of illustrations, not all elements and components depicted and labeled in one drawing are necessarily labels in another drawing even if these elements and components appear in such other drawing.

While various modifications and alternative forms, of implementation of the idea of the invention are within the scope of the invention, specific embodiments thereof are shown by way of example in the drawings and are described below in detail. It should be understood, however, that the drawings and related detailed description are not intended to limit the implementation of the idea of the invention to the particular form disclosed in this application, but on the contrary, the intention is to cover all modifications, equivalents and alternatives falling within the spirit and scope of the present invention as defined by the appended claims.

DETAILED DESCRIPTION OF THE INVENTION

In FIG. 1, a sectional view of a disk-type rotary joint 100 is shown. The rotary joint has a center axis 110 which is the rotation axis of the rotary joint. Orthogonal to the center axis 110 is a plane of rotation 105. This may roughly be a plane of symmetry between a first part 200 and a second part 300 rotating against each other. In this Figure, the first part 200 of the rotary joint is above the plane of rotation 105, whereas the second part 300 of the rotary joint is below the plane of rotation 105. The first part 200 may include a first magnetic core 210, further including at least one first winding 212. The first winding 212 may include a plurality of wires or cables which may be insulated against each other and which may be wound in or around the magnetic core. In this embodiment, the magnetic core is a U-shaped core. The magnetic core may also be an E-shaped core or may have any other suitable shape. To provide a good coupling between the first part and the second part, the first magnetic core 210 and the second magnetic core 310 could form a closed magnetic circuit with minimal air gaps 211 between them. Such air gaps are hardly to avoid because the first part is rotatable against the second part. If the air gap is closed, there would be a high friction. Normally, there is a circular air gap 211 (with the width indicated as 244), which is formed between the at least one first magnetic core 210 and the at least one second magnetic core 310.

The first part of the rotary joint further includes at least one first capacitive data link component 270, and the rotary joint may further include an alternate first capacitive data link component 280. All these parts may be held and/or contained on a first printed circuit board (PCB) 250.

The second part 300 includes a second magnetic core 310 further including a second winding 312, which may be like the first winding 212. If a change in voltage between the input and output voltage of the rotating transformer is desired, there may be different numbers of windings in the first winding 212 and the second winding 312. Further, the second part may further include a second capacitive data link component 370 as well as an optional alternate second capacitive data link component 380. All these parts may be held by or integrated into a second printed circuit board (PCB) 350.

Further, at least one resonant shield 400 is provided outside the airgap. There may be multiple resonant shields. Here, a resonant shield 400 is shown at the first printed circuit board (PCB) 250 and another resonant shield 400 is shown at the second printed circuit board (PCB) 350.

As the resonant shield is placed close to the magnetic cores, stray fields from the magnetic cores will generate eddy currents in the sliding track and therefore these magnetic stray fields will be weakened. Accordingly, the presence of the sliding track weakens the stray fields.

In this figure, the width 241 of first magnetic core 210, the height 242 of first magnetic core 210 and the distance of an open ring shaped structure 400 at the first PCB 250 is indicated. Also, the width 341 of second magnetic core 310, the height 342 of second magnetic core 310 and the distance of an open ring shaped structure 400 at the second PCB 350 is indicated. The resonance shields have the best effect, if the corresponding open ring shaped structures are comparatively close to the source of the magnetic field. Tests have shown that the open ring shaped structures may be closer to a magnetic core than a maximum dimension of a magnetic core for best efficiency. Efficiency is further increased, if the distance between the open ring shaped structures and an air gap is closer than one of 10 times, 5 times, 2 times the size of the air gap. Numerals 243 and 343 indicate, respectively, a distance between the resonant shield 400 of the first PCB 250 and the first magnetic core 210 and a distance between the resonant shield 400 of the second PCB 350 and the second magnetic core 310. In at least one case, a distance 245. separating the resonance shield of the first PCB and the resonant shield of the second PCB 350, is greater than the width of the airgap 244.

Figure 2:
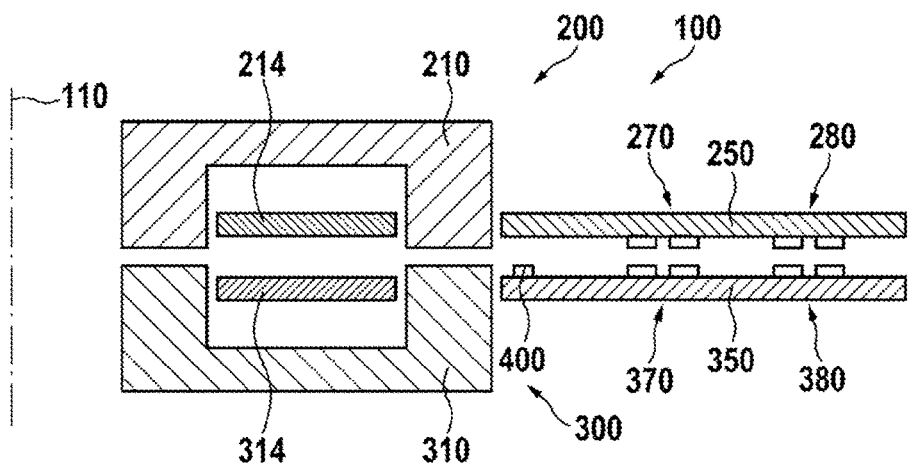
FIG. 2 shows a different embodiment.

In FIG. 2, a different embodiment is shown, where instead of wires of the first winding 212 and the second winding 312 as shown in FIG. 1, printed circuit boards 214 and 314 are used. Making a coil structure on printed circuit boards is a much simpler and more inexpensive manufacturing process compared to manually winding wires into the magnetic cores. Such printed circuit board traces normally have a lower current capacity compared to solid copper wires, but these traces can be used in many applications, specifically where a comparatively low power is coupled. If a lower power is coupled, the magnetic cores may further be reduced in size, which further leads to a reduction in total size of the rotary joint.

The coil structure of the power transmission may be a stack of multilayer windings which are cascaded and interconnected by vias to get a larger number of windings.

Figure 3:
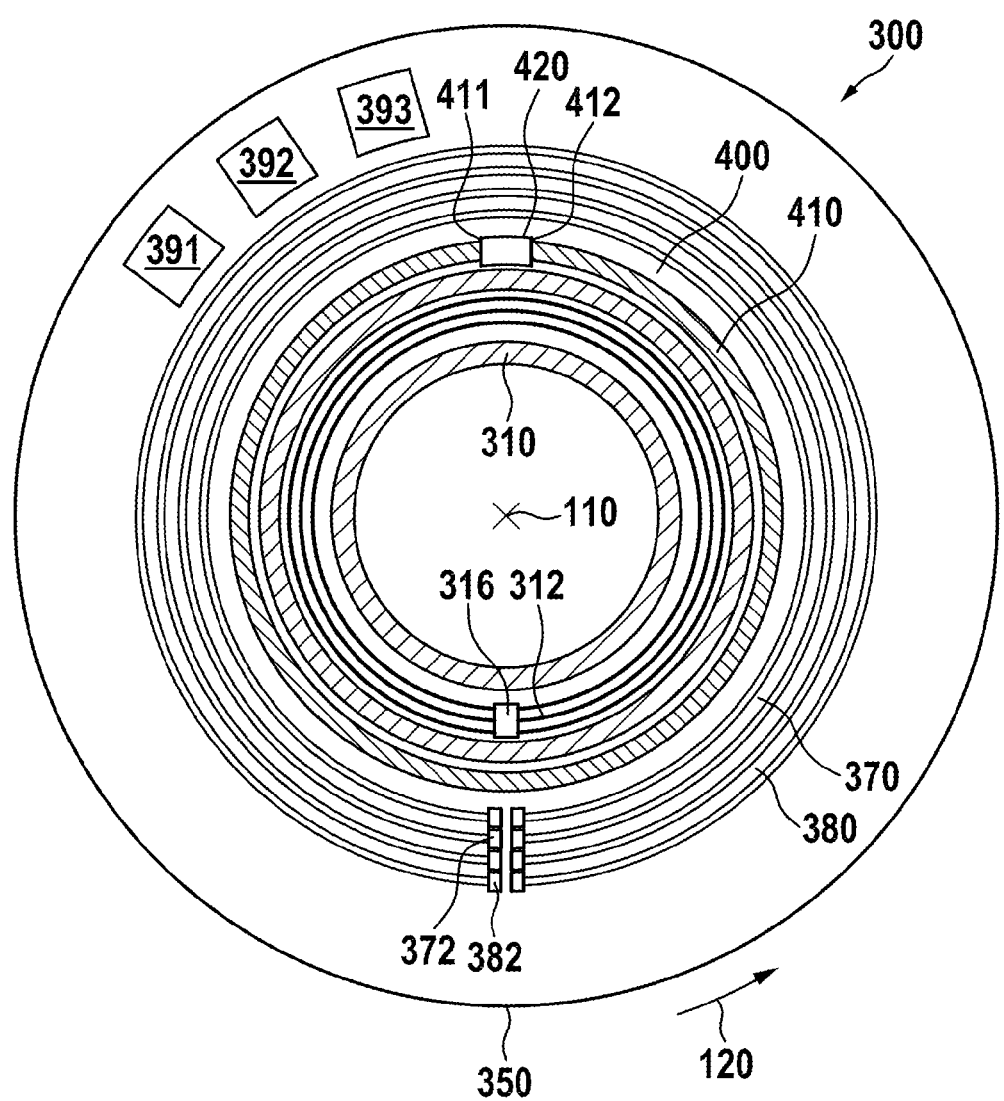
FIG. 3 shows a top view of an embodiment.

In FIG. 3, a top view of an embodiment of the second part 300 is shown. This Figure is further showing many features previously explained in FIGS. 1 and 2. In addition, a winding termination 316 for the second winding is shown. This winding termination may be an opening or a duct through which the winding is extended out of the magnetic core. The second magnetic core 310 is shown as one piece. In an embodiment, the first magnetic core 210 (FIG. 1) and/or the second magnetic core 310 may be made of multiple pieces or segments. Further, a second capacitive data link termination 372 is shown, which terminates the lines of the second capacitive data link component 370. An alternate second capacitive data link termination 382 may be provided to terminate the lines of the alternate second capacitive data link component 380. The arrow 120 indicates a possible direction of rotation, although the part 300 may rotate in an opposite direction or may rotate alternatingly. There may be further electrical and/or electronic components 391, 392 and 393 which may include at least one of a connector, an amplifier, a signal processing device and a microcontroller.

This figure further shows a resonant shield 400 which includes an open ring shaped structure 410, having two open ends 411, 412 which are connected by a capacitor 420 to form a resonant circuit.

Figure 4:
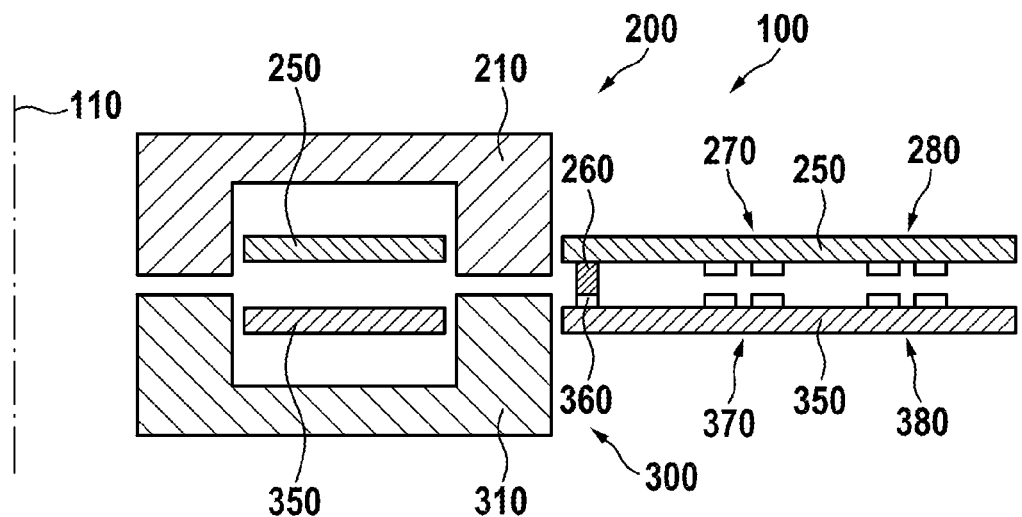
FIG. 4 shows an embodiment with a single PCB.

In FIG. 4, an embodiment with a single printed circuit board (PCB) 250 at the first part and a single PCB 350 at the second part is shown. Here, the first PCB 250 penetrates the magnetic core 210 to provide the windings therein. Also, the second PCB 350 penetrates the second magnetic core 310 to provide further windings therein. For the penetrations of the PCB into the cores, the cores may have at least one cutout.

The first part of the rotary joint may further include at least one sliding brush 260, which may be a carbon brush or a metal brush, further, the second part may include at least one sliding track 360. As shown in FIG. 4, the galvanic slipring system including the sliding brush 260 and the sliding track 360 may be arranged in radial direction with respect to the rotation axis 110 between the first magnetic core_210 and second magnetic core_310 and the first capacitive data link component 270 and second capacitive datalink component_370. In a radial direction, the galvanic slipring components may be arranged outside of the magnetic cores and inside of the capacitive data link components. The at least one sliding track 360 may be a low resistance track designed for high current capability_and have a width wider than the distance 245 between the at least one first magnetic core and the at least one second magnetic core, and/or have a width wider than at least one of 2 mm, 5 mm, 8 mm, 10 mm, and 15 mm and narrower than at least one of 50 mm, 40 mm, 30 mm, 20 mm, 10 mm, and/or have at least one galvanized layer configured for reducing contact resistance.

Figure 5:
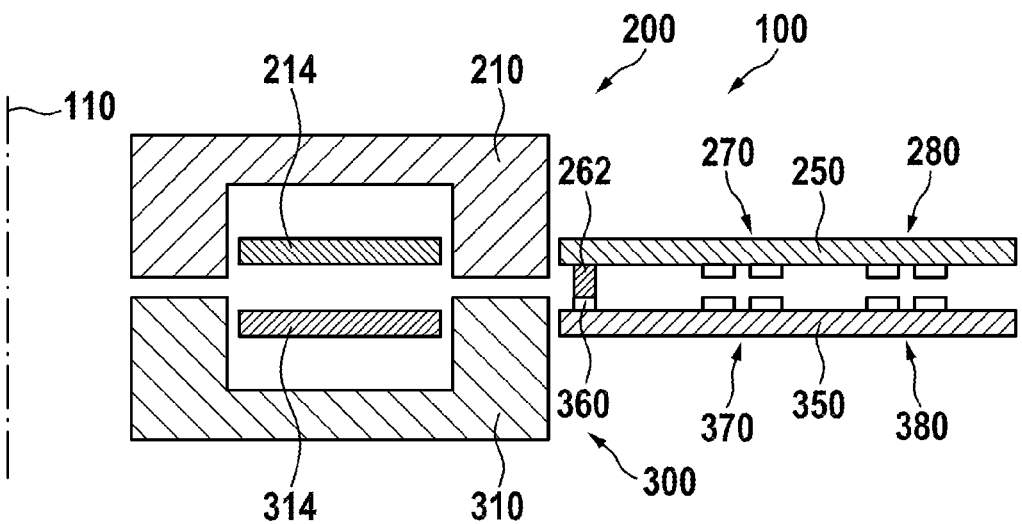
FIG. 5 shows an embodiment with a metal spring brush.

In FIG. 5, an embodiment with a metal spring brush is shown. Here, a flat metal spring brush 262 is provided for contacting the sliding track 360. Details of the brush are shown in the next figure.

Figure 6:
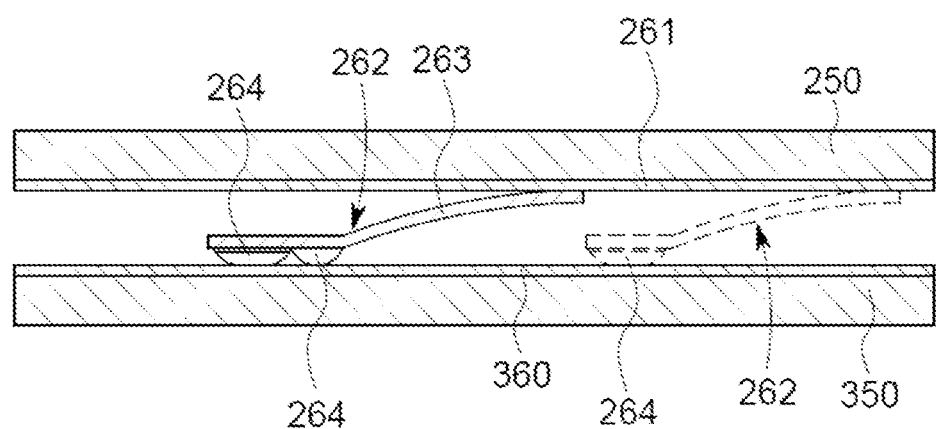
FIG. 6 shows details of a metal spring brush.

In FIG. 6, further details of a metal spring brush contact system are shown. At the bottom of this Figure is second PCB 350 with sliding track 360 thereon. Opposing thereto is first PCB 250 with a flat metal spring brush 262 attached. This brush 262 may be attached by soldering, welding, riveting, or a combination thereof or any other suitable attachment process which provides a good electric galvanic contact between the flat metal spring brush and at least one conductive trace on the printed circuit board 250. The flat metal spring brush 262 includes a metal spring 263 which may be made out of sheet metal or of a wire and which may include a contact element 264 at an end distant from the other end attached to the printed circuit board. This contact element 264 may be an extra plating at the flat metal spring brush, for example a gold or silver plating to increase conductivity and contact properties. It may also be an extra piece of metal or carbon or any other conductive material attached to the metal spring 263. There may be a circular conductive track 261 on the first PCB 250 for contacting the sliding brush 262. This track would provide further shielding and would provide a good electrical contact. Further, there may be multiple flat metal spring brushes 262 connected to said track and arranged on a circle around the center axis 110. Optionally multiple brushes 262 and contact elements 264 are shown in dashed lines. This arrangement provides best shielding characteristics, if the distance (or gap) in an axial direction between the electrically conductive track 261 and the sliding track 360 is less or equal than an air gap 211 between the magnetic cores 210, 310 as shown in FIG. 1. Multiple brushes may improve the contact performance, such as decreasing contact resistance and decreasing contact noise.

Figure 7:
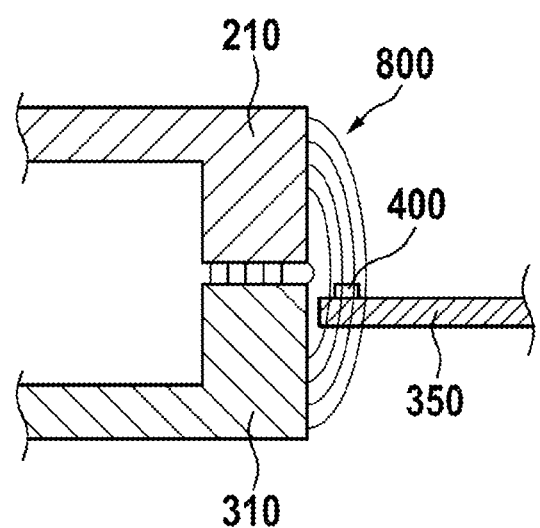
FIG. 7 shows magnetic fields of the magnetic cores in details.

In FIG. 7, details of the magnetic fields of the magnetic cores are shown. The Figure shows enlarged a first magnetic core 210 and a second magnetic core 310. There are always magnetic fields 800 outside of the magnetic cores. These fields are also referred to as stray fields. At low flux within the magnetic core, these outside stray fields are comparatively weak. If the flux in the core is increased and is approaching saturation of the core, stray fields increase. Such increase may lead to unacceptable high magnetic fields outside of the magnetic core, which may interfere with the capacitive data links. Therefore, a resonant shield 400 is provided between the capacitive data links and the magnetic cores, such that the magnetic field in the sliding track generates eddy currents which lead to weakening of the magnetic fields. As mentioned before, opposing to resonant shield 400, there may be another resonant shield 400 on first PCB 250 (FIG. 4) for contacting at least one sliding brush or multiple sliding brushes.

Figure 8:
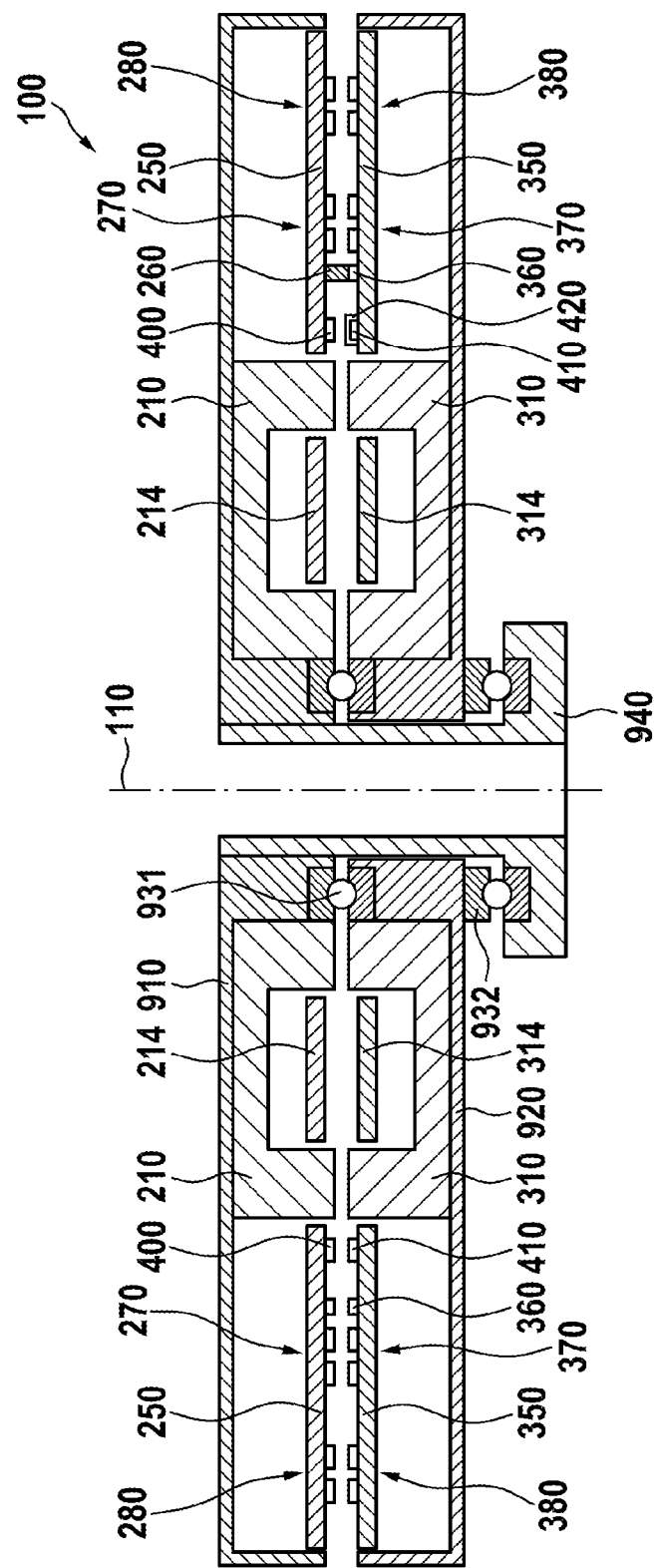
FIG. 8 shows an example of a housing with an integrated rotary joint.

In FIG. 8, an example of a housing with an integrated rotary joint is shown. Here, the components described before are integrated into a housing including a first housing section 910 and a second housing section 920. The first housing section 910 holds the first part 200 (shown in FIG. 5), whereas the second housing section 920 holds the second part 300 (shown in FIG. 5). There may be at least a first bearing 931 between the first housing section 910 and the second housing section 920 to hold these in a well-defined position relative to each other while allowing for rotation. There may be a second bearing 932 for stabilizing the assembly. First bearing 931 and second bearing 932 may be at least one of a ball bearing, a slide bearing, or any other suitable bearing. There may be a housing connector 940 which for example may be fixedly connected to the first housing section 910, for example by a thread and which may be rotatable against the second housing section 920, thus providing a gap thereto. This housing connector 940 may further serve to hold first bearing 931 and/or second bearing 932 in place. The first part may be held by additional studs, screws, clips, or other mounting devices within the first housing section, and the second part may be held by similar parts in the second housing section. Further a resonant shield 400 is shown at each PCB, having an open ring shaped structure 410 and a capacitor 420.

Thermal pads or thermally conductive glue or paste or thermally conductive compounds may bridge the gap between housing and components, housing and ferrite cores. The cores may be fixed by glue to the PCB.

While FIG. 8 shows a bearing the housing can be used without bearing when both parts are mounted with the housing as mechanical interface within a customer system. Elements mounted to the PCB might serve as parts for the fixation of the housing and connecting the housing with potentials on the PCB, e.g. the brush track. There may be pads for electronic components e.g. at least one resistor or capacitor.

Figure 9:
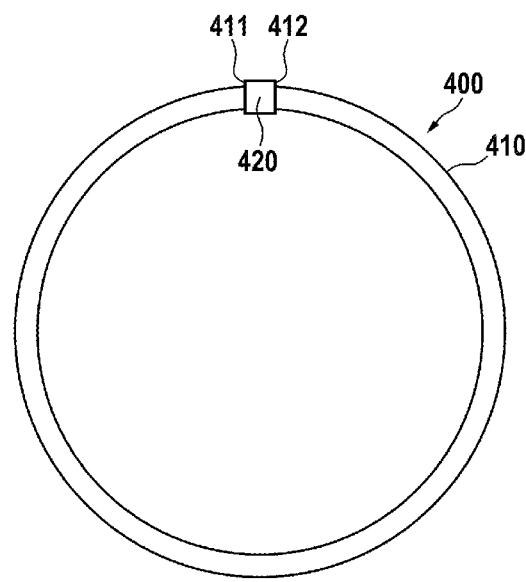
FIG. 9 shows a resonant shield.

FIG. 9 shows a resonant shield 400 which includes an open ring shaped structure 410, having two open ends 411, 412 which are connected by a capacitor 420 to form a resonant circuit. A resistor may be connected in parallel or in series to the ring shaped structure or the capacitor. Also, a capacitor with losses at the resonance frequency may be used to increase damping of the resonance circuitry thereby widening the frequency range where a low impedance of the resonance shield is achieved.

Also a resonant shield may be a parallel or serial connection of multiple circular tracks as open ring structures in a multilayer printed circuit board which may be interconnected by vias. There may be pads on the outer layer (component side) for electronic components e.g. at least one resistor or capacitor.

Figure 10:
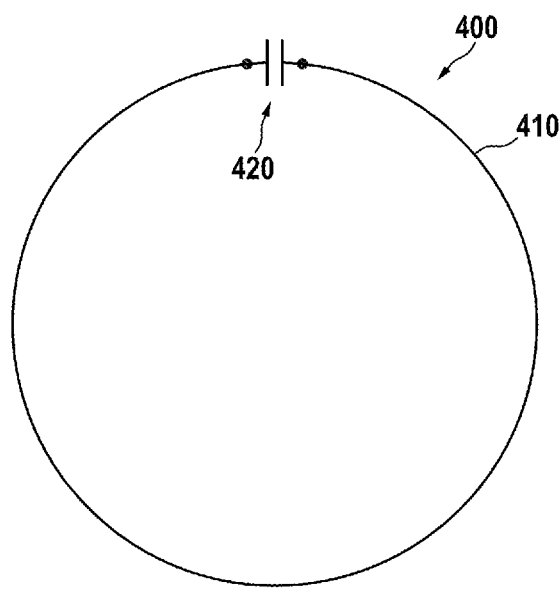
FIG. 10 shows a circuit diagram of a resonant shield

FIG. 10 shows a circuit diagram of a resonant shield 400. The capacitor 420 forms together with the inductance of the open ring shaped structure 410 a resonant circuit.

Figure 11:
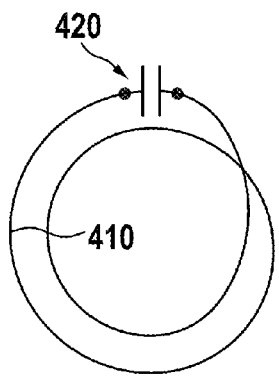
FIG. 11 shows a circuit diagram with two turns.

FIG. 11 shows a circuit diagram of a resonant having an open ring shaped structure with two turns. Generally, the open ring structure may have any number of turns. Embodiments with a plurality of turns may be combined with other embodiments disclosed herein, e.g. combined with a resistor 430 (as identified below in FIG. 12) and/or an inductor 440 (as identified below in FIG. 15). In an embodiment with two or more turns, a smaller capacitor 420 may be used.

Figure 12:
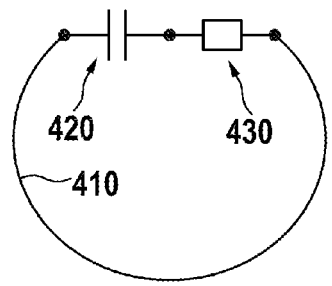
FIG. 12 shows a circuit diagram with a resistor connected in series.

FIG. 12 shows a circuit diagram with a resistor 430 connected in series with the capacitor 420, which may increase damping and therefore decrease the Q factor which would result in an increased bandwidth.

Figure 13:
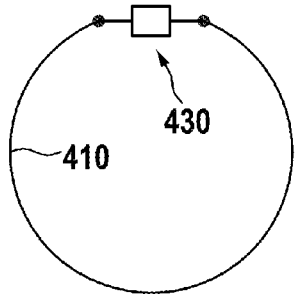
FIG. 13 shows a circuit diagram with a resistor only.

FIG. 13 shows a circuit diagram with a resistor 430 only. The resistor gives a broadband attenuation.

Figure 14:
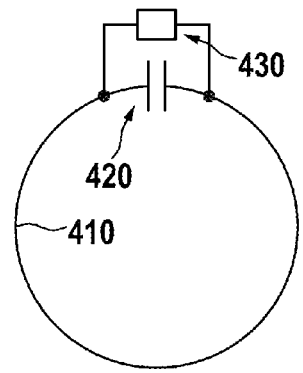
FIG. 14 shows a circuit diagram with a resistor connected parallel.

FIG. 14 shows a circuit diagram with a resistor 430 added and connected parallel to the capacitor 420 and the open ring shaped structure 410, which may increase damping and therefore decrease the Q factor which would result in an increased bandwidth.

Figure 15:
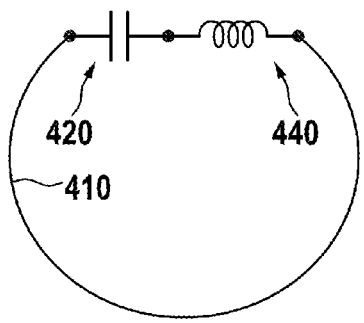
FIG. 15 shows a circuit diagram with an additional inductor 440 connected in series.

FIG. 15 shows a circuit diagram with an inductor 440 connected in series with a capacitor 420, which results in a lower resonant frequency, such that a smaller capacitor may be required.

Figure 16:
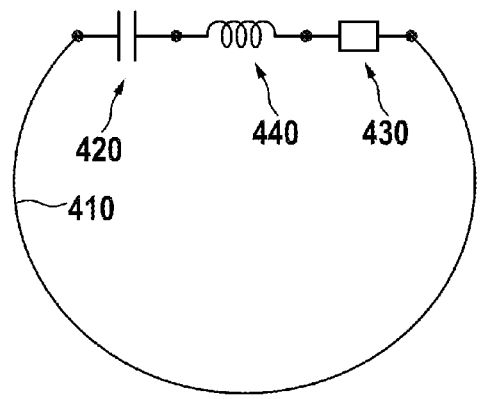
FIG. 16 shows a circuit diagram with a further resistor 430 connected in series.

FIG. 16 shows a further circuit diagram with a resistor 430 connected in series with the capacitor 420, the inductor 440, and the open ring shaped structure 410. This resistor may increase damping and therefore decrease the Q factor which would result in an increased bandwidth.

Figure 17:
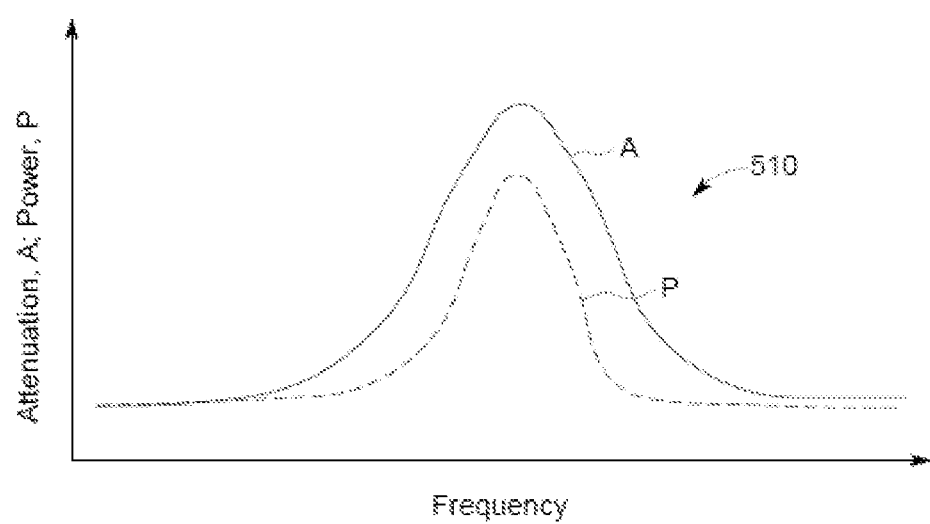
FIG. 17 shows an attenuation diagram.

FIG. 17 shows an attenuation diagram 510 with a field attenuation curve A of a resonant shield and a characteristic power transformer output power B which is depending on the operating frequency and may have its maximum in the same frequency range as the attenuation curve A. The diagram has a horizontal frequency axis and a vertical attenuation axis (curve A) and power axis (curve B). The width of the attenuation curve A may be increased by adding losses, e.g. by adding a resistor or a capacitor with losses as mentioned above.

Figure 18:
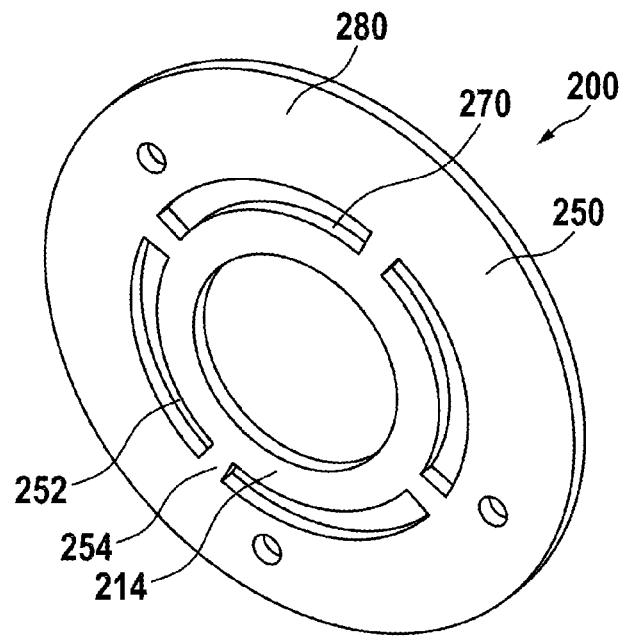
FIG. 18 shows a PCB in a perspective view.

FIG. 18 shows a first PCB 250 in a perspective view. The PCB may have webs 254 and cutouts 252. The magnetic cores—for example, the core 210 (FIG. 19)—may have cutouts, which may be arranged so that these cutouts interlock with the webs and cutouts of the PCB. The webs of the PCB may be connecting mechanically and electrically the winding part of the PCB and the part carrying the components of the capacitive link and further electronics required.

Figure 19:
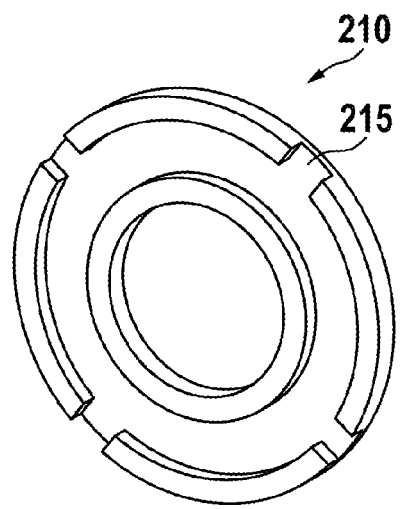
FIG. 19 shows a magnetic core in a perspective view.

FIG. 19 shows a magnetic core in a perspective view. This magnetic core has 4 cutouts 215.

Figure 20:
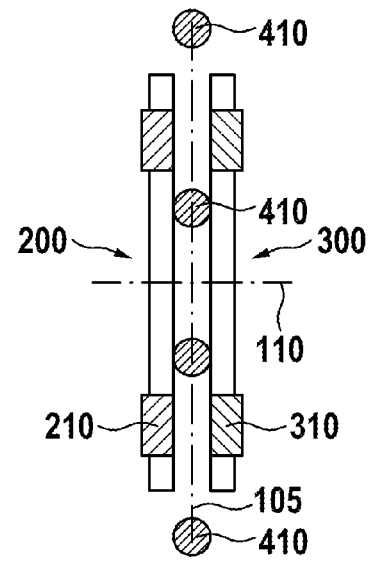
FIG. 20 schematically shows a disk arrangement.

FIG. 20 schematically depicts a disk arrangement, where the rotating parts have a disk shaped interface. The first rotating part 200 is arranged on an opposing side of a plane of rotation 105 against the second rotating part 300. The plane of rotation 105 is orthogonal to the rotation axis 110. The first rotating part 200 bears first magnetic core 210 and the second rotating part 300 bears second magnetic core 310. An open ring shaped structure 410 may be arranged in axial direction outside and/or inside of the first and second magnetic cores which are shown here disk shaped with a free inner bore.

Figure 21:
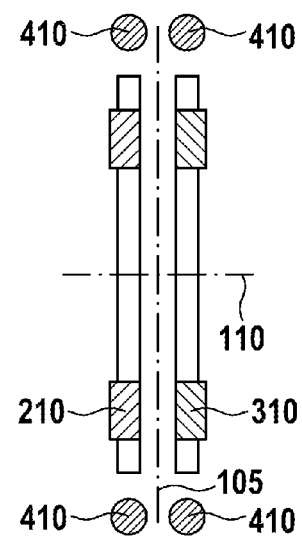
FIG. 21 schematically shows a further disk arrangement.

FIG. 21 illustrates a similar embodiment as the previous figure, but now two open ring shaped structure 410 may be provided. One may be on each rotating side. This further increases attenuation of magnetic fields.

Figure 22:
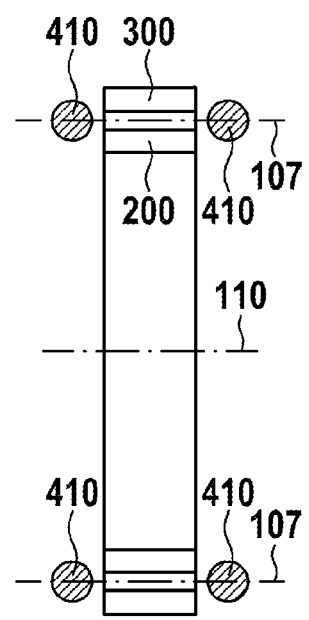
FIG. 22 schematically shows a drum arrangement.

FIG. 22 schematically shows a further embodiment of a drum or cylinder arrangement. Here, the rotating parts rotate about a cylinder 107 around the rotation axis 110. At least one open ring shaped structure 410 may be provided axially outside the airgap of the magnetic cores on either side or both sides. Here, also two or more open ring shaped structures 410 may be provided.

It will be appreciated to those skilled in the art having the benefit of this disclosure that this invention is believed to provide a compact rotary joint. Further modifications and alternative embodiments of various aspects of the invention will be apparent to those skilled in the art in view of this description. Accordingly, this description is to be construed as illustrative only and is provided for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS 100 rotary joint
105 plane of rotation
107 cylinder of rotation
110 rotation axis
120 direction of rotation
200 first part
210 first magnetic core
211 air gap
212 first winding
214 first winding on PCB
215 first magnetic core cutout
241 width of first magnetic core
242 height of first magnetic core
243 distance to first magnetic core
244 width of the airgap 211
245 distance separating the resonant shields
250 first PCB
252 first PCB cutout
254 first PCB web
260 sliding brush
261 conductive track
262 flat metal spring brush
263 metal spring
264 contact element
270 first capacitive data link component
280 alternate first capacitive data link component
300 second part
310 second magnetic core
312 second winding
314 second winding on PCB
316 winding termination
341 width of second magnetic core
342 height of second magnetic core
343 distance to second magnetic core
350 second PCB
360 sliding track
370 second capacitive data link component
372 second capacitive data link termination
380 alternate second capacitive data link component
382 alternate second capacitive data link termination
391-393 electronic components
400 resonant shield
410 open ring shaped structure
411, 412 open ends
415 open ring shaped structure with multiple turns
420 capacitor
430 resistor
440 inductor
510 attenuation diagram
511 field attenuation curve of resonance shield
512 power transformer output power
800 magnetic stray field
910 first housing section
920 second housing section
931 first bearing
932 second bearing
940 housing connector

The invention claimed is:

1. A rotary joint comprising
a first part and a second part, the second part configured to rotate around a rotation axis against the first part,
wherein the first part includes at least one first magnetic core, the second part includes at least one second magnetic core configured for coupling power with the at least one first magnetic core,
wherein a first winding is within the at least one first magnetic core, and a second winding is within the at least one second magnetic core, the first winding and the second winding are magnetically coupled with each other through the at least one first magnetic core and the at least one second magnetic core,
wherein a circular air gap is formed between the at least one first magnetic core and the at least one second magnetic core,
wherein at least one resonant shield is provided outside one or more of the at least one first magnetic core and the at least one second magnetic core and outside of the airgap, and
wherein the at least one resonant shield comprises an open ring shaped structure having two open ends, the two open ends being connected by a capacitor to form a resonant circuit.

2. A rotary joint according to claim 1, wherein the at least one resonance shield is configured to cancel more than 50% or more than 60% or more than 70% or more than 80% or more than 90% or more than 95% of a stray field from the airgap and/or a stray field from the at least one first magnetic core or the at least one second magnetic core.

3. A rotary joint according to claim 1, wherein a resonance frequency of the at least one resonance shield is either equal to an operational frequency of the at least one first magnetic core and the at least one second magnetic core or multiples thereof, or deviates from such operational frequency or said multiples thereof by less than 20%.

4. A rotary joint according to claim 1, wherein
the first part and the second part are arranged on opposing sides of a common plane that is orthogonal to the rotation axis.

5. A rotary joint according to claim 1, wherein
the rotary joint is a disc-type rotary joint,
the first part further includes at least one sliding brush,
the second part further includes at least one sliding track configured for galvanic coupling with the at least one sliding brush, and
wherein the at least one sliding track is arranged radially between the at least one second magnetic core and at least one second data link component of the rotary joint.

6. A rotary joint according to claim 5,
wherein the first part includes at least one first data link component, and the second part includes the at least one second data link component configured to transfer data from and/or to the at least one first data link component,
wherein the least one first data link component and the at least one second data link component are at least one of capacitive datalink components, inductive datalink components, and wireless components.

7. A rotary joint according to claim 6, wherein
(a) the at least one sliding track has a width wider than a distance between the at least one first magnetic core and the at least one second magnetic core, and/or
(b) the at least one sliding track has a width wider than at least one of 2 mm, 5 mm, 8 mm, 10 mm, and 15 mm and narrower than at least one of 50 mm, 40 mm, 30 mm, 20 mm, 10 mm, and/or
(c) the at least one sliding track has at least one galvanized layer configured for reducing contact resistance.

8. A rotary joint according to claim 7, wherein the at least one galvanized layer includes at least one of gold and silver.

9. A rotary joint according to claim 1, wherein
the first part includes a first printed circuit board that further includes an electrically conductive track arranged at the same radial position as a sliding track and that is electrically connected to at least one sliding brush, wherein an axial distance between the electrically conductive track and the sliding track is shorter than or equal to the air gap between the at least one first magnetic core and the at least one second magnetic core.

10. A rotary joint according to claim 9, wherein the electrically conductive track has multiple electrical contacts to the sliding track.

11. A rotary joint according to claim 9,
wherein the electrically conductive track at the first printed circuit board has the same width as that of the sliding track, and/or
wherein the sliding track is arranged below a plane defined by the air gap between the at least one first magnetic core and the at least one second magnetic core.

12. A rotary joint according to claim 11, wherein the at least one sliding brush is mounted above the plane.

13. A rotary joint according to claim 1, wherein
the at least one resonant shield includes two or more resonance shields that are spaced apart from each other, and wherein a distance separating a first resonance shield of the at least one resonant shield from a second resonant shield of the at least one resonant shield is equal to or greater than a width of the airgap.

14. A rotary joint according to claim 1, wherein
a distance between the open ring shaped structure of the at least one resonant shield and the air gap is shorter than at least one of 10 times a size of the air gap, 5 times the size of the air gap, and 2 times the size of the air gap.

15. A rotary joint according to claim 1, wherein
the at least one resonant shield is mounted to the first part at a first distance relative to the at least one first magnetic core, said first distance being shorter than the larger of a width and a height of the at least one first magnetic core, and/or
the at least one resonant shield is mounted to the second part at a second distance relative to the at least one second magnetic core, said second distance being shorter than the larger of a width and a height of the at least one second magnetic core.

16. A rotary joint according to claim 1, wherein
the rotary joint is a drum or cylinder type rotary joint and the at least one resonant shield is separated from the at least one first magnetic core and/or the at least one second magnetic core along the rotation axis.

17. A rotary joint according to claim 1, wherein
the rotary joint is a disk type rotary joint and the at least one resonant shield is arranged radially outside of at least one first magnetic core and/or the at least one second magnetic core.

\* \* \* \* \*